United States Patent
Marsh et al.

(10) Patent No.: US 10,695,503 B2
(45) Date of Patent: Jun. 30, 2020

(54) DRIVE SLEEVE, DRUG DELIVERY DEVICE AND METHOD FOR ASSEMBLING A DRUG DELIVERY DEVICE

(71) Applicant: Sanofi, Paris (FR)

(72) Inventors: William Marsh, Buckinghamshire (GB); Anthony Paul Morris, Coventry (GB)

(73) Assignee: Sanofi, Paris (FR)

( * ) Notice: Subject to any disclaimer, the term of this patent is extended or adjusted under 35 U.S.C. 154(b) by 366 days.

(21) Appl. No.: 15/515,046

(22) PCT Filed: Oct. 9, 2015

(86) PCT No.: PCT/EP2015/073428
§ 371 (c)(1),
(2) Date: Mar. 28, 2017

(87) PCT Pub. No.: WO2016/055623
PCT Pub. Date: Apr. 14, 2016

(65) Prior Publication Data
US 2019/0054249 A1 Feb. 21, 2019

(30) Foreign Application Priority Data
Oct. 9, 2014 (EP) ..................................... 14306589

(51) Int. Cl.
*A61M 5/31* (2006.01)
*A61M 5/315* (2006.01)
(Continued)

(52) U.S. Cl.
CPC .......... *A61M 5/31553* (2013.01); *A61M 5/20* (2013.01); *A61M 5/24* (2013.01);
(Continued)

(58) Field of Classification Search
CPC .......... A61M 5/31533; A61M 5/31545; A61M 5/31548; A61M 5/3155; A61M 5/31551; A61M 5/31563
See application file for complete search history.

(56) References Cited

FOREIGN PATENT DOCUMENTS

| EP | 1642607 | 4/2006 |
|---|---|---|
| WO | WO 2006/037434 | 5/2006 |

(Continued)

OTHER PUBLICATIONS

Information Disclosure Statement and Written Opinion in International Application No. PCT/EP2015/073428, dated Dec. 15, 2015, 11 pages.

(Continued)

*Primary Examiner* — William R Carpenter
(74) *Attorney, Agent, or Firm* — Fish & Richardson P.C.

(57) ABSTRACT

The present disclosure is directed to a drive sleeve with a hollow body having a ring of crown teeth with a first outer diameter forming a clutch interface at a first end and a thread extending on an outer surface of the body. The thread has a major diameter and a minor diameter, wherein the ring of crown teeth has at least two cavities. The at least two cavities extend on the outer surface of the body from the first end to the thread and defining a second outer diameter which is smaller than the major diameter of the thread. Further, some embodiments are directed to a drug delivery device with such a drive sleeve and a method for assembling a drug delivery device.

13 Claims, 2 Drawing Sheets

(51) Int. Cl.
*A61M 5/24* (2006.01)
*A61M 5/20* (2006.01)
(52) U.S. Cl.
CPC .... *A61M 5/31541* (2013.01); *A61M 5/31563* (2013.01); *A61M 5/31583* (2013.01); *A61M 5/31593* (2013.01); *A61M 2005/3126* (2013.01); *A61M 2205/581* (2013.01); *A61M 2205/582* (2013.01); *A61M 2205/583* (2013.01); *A61M 2207/00* (2013.01)

(56) References Cited

FOREIGN PATENT DOCUMENTS

| WO | WO 2012/049141 | 4/2012 | | |
|---|---|---|---|---|
| WO | WO 2012/130705 | 10/2012 | | |
| WO | WO-2014033195 A1 * | 3/2014 | .............. | A61M 5/24 |
| WO | WO 2014/166908 | 10/2014 | | |

OTHER PUBLICATIONS

International Preliminary Report on Patentability in International Application No. PCT/EP2015/073428, dated Apr. 11, 2017, 7 pages.

* cited by examiner

DRIVE SLEEVE, DRUG DELIVERY DEVICE AND METHOD FOR ASSEMBLING A DRUG DELIVERY DEVICE

CROSS-REFERENCE TO RELATED APPLICATIONS

This application is a U.S. national stage application under 35 USC § 371 of International Application No. PCT/EP2015/073428, filed on Oct. 9, 2015, which claims priority to European Patent Application No. 14306589.4 filed on Oct. 9, 2014, the entire contents of which are incorporated herein by reference.

TECHNICAL FIELD

The present disclosure is generally directed to a drive sleeve, e.g. for a drug delivery device for selecting and dispensing a number of user variable doses of a medicament. Further, the disclosure is directed to a drug delivery device with such a drive sleeve and a method for assembling a drug delivery device.

BACKGROUND

Pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament. Some embodiments are not directed to so called fixed dose devices which only allow dispensing of a predefined dose without the possibility to increase or decrease the set dose.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism. Some embodiments are directed to reusable devices which allow resetting of the device and a replacement of a cartridge. Resetting of the device typically involves moving a piston rod or lead screw from an extended (distal) position, i.e. a position after dose dispensing, into a more retracted (proximal) position.

These types of pen delivery devices (so named because they often resemble an enlarged fountain pen) generally comprise three primary elements: a cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the pen device that is used to set (select) a dose. During an injection, a spindle or piston rod contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

A further differentiation of drug delivery device types refers to the drive mechanism: There are devices which are manually driven, e.g. by a user applying a force to an injection button, devices which are driven by a spring or the like and devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting.

SUMMARY

In some embodiments an advantage may be providing a drive sleeve with a clutch interface at one end allowing easy assembly with a complete nut.

A drive sleeve has a hollow body having a clutch interface at a first end and a thread extending on an outer surface of the body. The clutch interface preferably comprises a ring of crown teeth with a first outer diameter. The thread has a major diameter and a minor diameter. To facilitate insertion of a full nut onto the drive sleeve, the ring of crown teeth has at least two cavities (cut-outs) extending on the outer surface of the body from the first end to the thread. The cavities define a second outer diameter which is smaller than the major diameter of the thread. In other words, the cavities allow attaching a full nut or even a sleeve for engaging the thread without interfering with the clutch interface. Providing the cavities or cut-outs reduces the outer diameter of the clutch interface only in relatively small sections of the drive sleeve body, whereas the rest of the clutch interface may still have a relatively large outer diameter. This larger outer diameter of the clutch interface is the most effective region for transmitting torque. Further, maximising the surface area of the clutch interface also reduces the clutch surface wear rates.

A drive sleeve is preferably an elongate hollow tube suitable to transmit a force and/or torque in a drug delivery device for selecting and dispensing a number of user variable doses of a medicament. A drive sleeve may be made from any suitable plastic material, e.g. by injection molding. A drive sleeve is typically movable at least during dispensing of a medicament rotationally and/or axially to thereby drive a further component part, such as a piston rod and/or a bung in a cartridge. The drive sleeve may be driven by one or more other component parts, e.g. via the clutch interface.

Preferably, the second outer diameter defined by the cavities is equal to or smaller than the minor diameter of the thread. For example, the cavities are slots extending in the axial direction of the body on its outer surface. This allows inserting a nut by a pure axial movement onto the drive sleeve and over the clutch interface, which facilitates the assembly process.

In a preferred embodiment the drive sleeve has four cavities or cut-outs. The cavities or cut-outs are preferably non-equispaced around the outer surface of the drive sleeve body. Thus, the nut or the like can be inserted onto the drive sleeve only in one or two predefined relative rotational positions. In addition, or as an alternative, the cavities or cut-outs may have different widths.

The crown teeth may be axially orientated and extending at a first end in a radial direction from an inner surface of the body to outer surface of the body. In other words, the crown teeth form one end, preferably the proximal end, of the drive sleeve body. This allows using the available diameter of the end face of the drive sleeve body for the clutch interface, thus maximising the surface available for transmitting torque. Axial orientation of the crown teeth may be understood as these are configured or, in particular, orientated to mesh in an axial direction with corresponding crown teeth on a second part. This, in instances, may be achieved by a profile radiating from an inner surface of the body to an outer surface of the body.

The clutch interface may be suitable to transmit a torque in one direction and to be overcome, i.e. slipping, in the opposite direction. This may be desirable in spring driven devices to react a spring torque and/or to provide different torque resistances depending on the direction of rotation. Such a clutch interface may comprise crown teeth with each tooth having a first ramp angle orientated in a first rotational direction and a second, steeper ramp angle orientated in a second, opposite rotational direction.

Preferably, at least one of the cavities or cut-outs ends in a start of the thread. For example, the thread is a double-start thread with one of the cavities ending in each start of the thread. This allows inserting a nut by a pure axial movement onto the drive sleeve and over the clutch interface such that the nut immediately engages the thread upon a relative rotation of the nut and the drive sleeve. Thus, no further assembly steps are required except axially putting the nut onto the drive sleeve.

To prevent an underdosage or a malfunction, a drug delivery device may comprise a last dose protection mechanism for preventing the setting of a dose, which exceeds the amount of liquid left in a cartridge. In a preferred embodiment, this last dose protection mechanism only detects the medicament remaining in the cartridge when the cartridge contains less than the maximum dose (e.g. 120 IU). For example, the last dose protection mechanism comprises a nut member located interposed between the drive sleeve and a component which rotates relative to the drive sleeve during dose setting and which does not rotate relative to the drive sleeve during dose dispensing. For such a last dose mechanism the drive sleeve may further comprise at least one rotational hard stop located at the end of the thread which is opposite to the ring of crown teeth. This rotational hard stop preferably interacts with the nut to prevent relative rotation between the component, e.g. a number sleeve, and the drive sleeve during dose setting.

Further, the hollow body of the drive sleeve may comprise at least one further clutch interface, e.g. with axially orientated splines located on the inner surface or the outer surface of the body. For example, the drive sleeve may comprise internal splines for rotationally coupling the drive sleeve to a piston rod. Further, a splined interface may be provided at the end opposite the crown teeth, i.e. preferably the distal end, for rotationally coupling the drive sleeve to a housing, e.g. during dose setting. Still further, there may be a splined interface on the outer surface of the drive sleeve for rotationally coupling and de-coupling the drive sleeve and a dose setting member and/or number sleeve.

In a preferred embodiment the drive sleeve as described above is a component part of a drug delivery device for selecting and dispensing a number of user variable doses of a medicament. Such a device may comprise in addition to the drive sleeve a housing, a dose setting member located within the housing, a piston rod engaging the drive sleeve, a clutch having a further a ring of crown teeth for rotationally coupling and de-coupling the drive sleeve and the dose setting member and/or a nut having at least one helical inner rib for engaging the thread of the drive sleeve. The drug delivery device may further comprise a cartridge containing a medicament.

Preferably, the width of the helical inner rib is equal to or smaller than the width of one of the cavities of the drive sleeve. This allows inserting the nut with the rib(s) onto the cavities or cut-outs of the drive sleeve. The use of small thread sections on the last dose nut minimises the size of the cut-outs in the drive sleeve clutch interface. These cut-outs extend from the outer diameter of the clutch interface which is the most effective region for transmitting torque. Therefore, by minimising the size of the cut-outs, the strength of the clutch interface is maximised.

According to a further aspect, a (last dose) nut is generally ring-shaped and comprises an internal thread, preferably in the form of a thread rib extending less than 360°, and axially extending splines, e.g. in the form of wings protruding from the ring form, preferably in the distal direction. The splines may be designed to axially guide the nut in a further component part, e.g. a number sleeve with internal axially extending grooves, to allow axial movement while preventing relative rotation. In addition to the wings further splines may be provided on the outer surface of the nut.

A method for assembling a drug delivery device preferably comprises the steps of providing a housing, a piston rod, a drive sleeve, a nut, a dose setting member and a clutch; inserting the nut onto the drive sleeve in an axial movement, whereby the at least one helical inner rib engages one of the cavities of the drive sleeve; and performing a relative rotational movement between the drive sleeve and the nut, until the at least one helical inner rib engages the thread of the drive sleeve. This provides a simple method for attaching a nut to the drive sleeve. The relative rotation may occur at a later point in time compared with the other assembly steps, for example during use.

Preferably, the method comprises the step of performing a test dispense after assembling the piston rod, the drive sleeve, the nut, the dose setting member and the clutch into the housing, wherein the relative rotational movement between the drive sleeve and the nut is performed during the test dispense.

The method may comprise the further step of engaging the nut with the dose setting member such that the nut is guided axially displaceable and rotationally constrained to the dose setting member.

The term "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin;

B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three on the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE DRAWINGS

Non-limiting, exemplary embodiments will now be described with reference to the accompanying drawings, in which.

DETAILED DESCRIPTION

Figure 1:
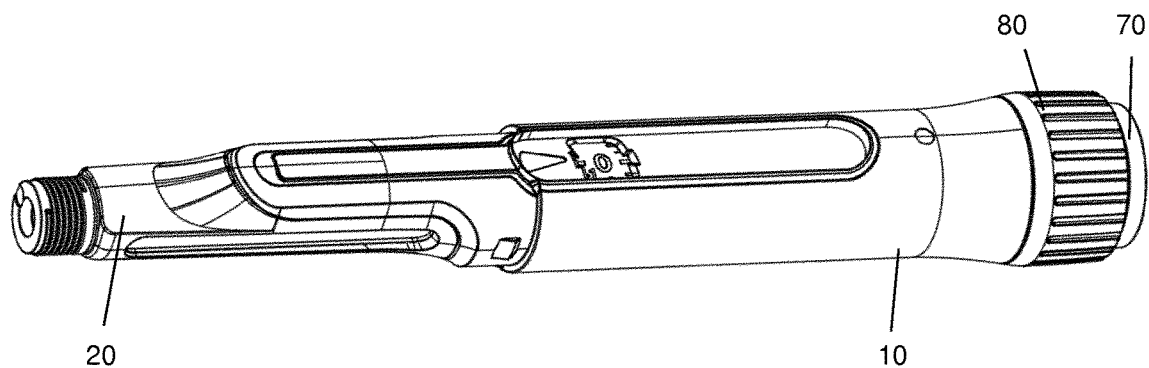
FIG. 1 shows a top view of a drug delivery device.
Figure 2:
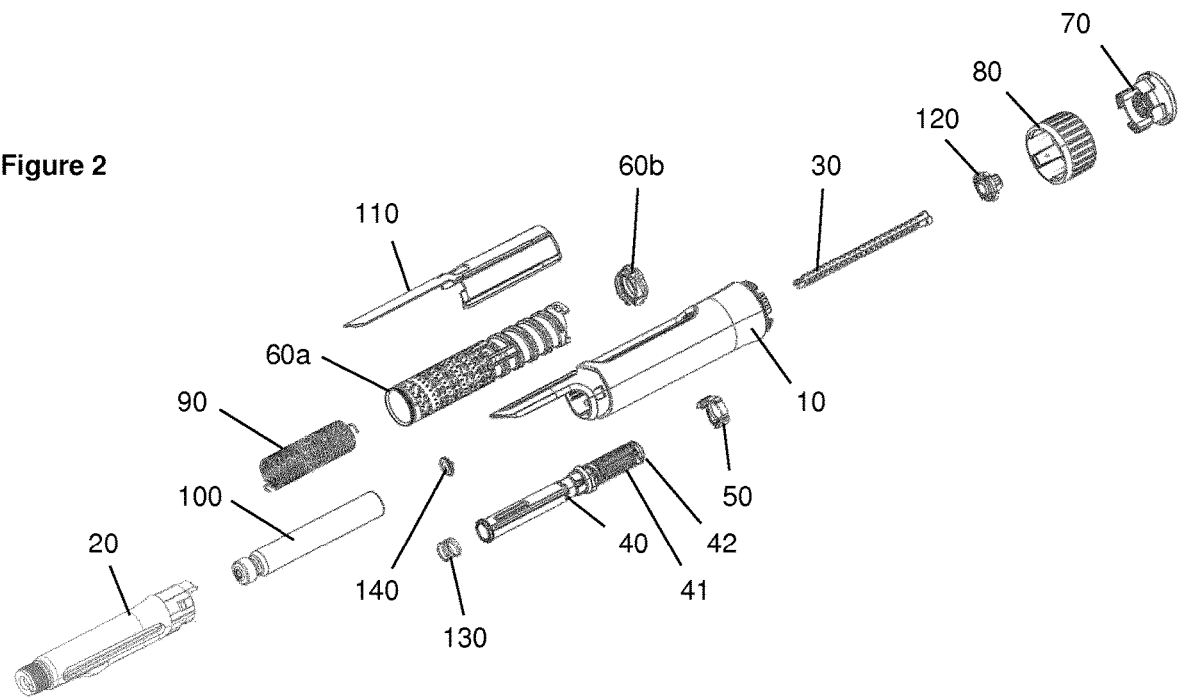
FIG. 2 shows an exploded view of the components of the device of FIG. 1.

FIG. 1 shows a drug delivery device in the form of an injection pen. The device has a distal end (left end in FIG. 1) and a proximal end (right end in FIG. 1). The component parts of the drug delivery device are shown in FIG. 2. The drug delivery device comprises a body or housing 10, a cartridge holder 20, a lead screw (piston rod) 30, a drive sleeve 40, a nut 50, a dose indicator (number sleeve) 60, a button 70, a dial grip or dose selector 80, a torsion spring 90, a cartridge 100, a gauge element 110, a clutch plate 120, a clutch spring 130 and a bearing 140. A needle arrangement (not shown) with a needle hub and a needle cover may be provided as additional components, which can be exchanged as explained above. All components are located concentrically about a common principal axis of the mechanism.

The housing 10 or body is a generally tubular element having a proximal end with an enlarged diameter. The housing 10 provides location for the liquid medication cartridge 100 and cartridge holder 20, windows for viewing the dose number on the number sleeve 60 and the gauge element 110, and a feature on its external surface, e.g. a circumferential groove, to axially retain the dose selector 80. An insert comprises an inner thread engaging the piston rod 30. The housing 10 further has at least one internal, axially orientated slot or the like for axially guiding the gauge element 110. In the embodiment shown in the Figures, the distal end is provided with an axially extending strip partly overlapping cartridge holder 20. The Figures depict the housing 10 as a single housing component. However, the housing 10 could comprise two or more housing components which may be permanently attached to each other during assembly of the device. The drive spring 90 is attached with one end to the housing 10.

The cartridge holder 20 is located at the distal side of housing 10 and permanently attached thereto. The cartridge holder may be a transparent or translucent component which is tubular to receive cartridge 100. The distal end of cartridge holder 20 may be provided with means for attaching a needle arrangement. A removable cap (not shown) may be provided to fit over the cartridge holder 20 and may be retained via clip features on the housing 10.

The piston rod 30 is rotationally constrained to the drive sleeve 40 via a splined interface. When rotated, the piston rod 30 is forced to move axially relative to the drive sleeve 40, through its threaded interface with the insert of housing 10. The lead screw 30 is an elongate member with an outer thread engaging the corresponding thread of the insert of housing 10. The interface comprises at least one longitudinal groove or track and a corresponding protrusion or spline of the driver 40. At its distal end, the lead screw 30 is provided with an interface for clip attachment of the bearing 140.

The drive sleeve 40 is a hollow member surrounding the lead screw 30 and arranged within number sleeve 60. It extends from an interface with the clutch plate 120 to the contact with the clutch spring 130. The drive sleeve 40 is axially movable relative to the housing 10, the piston rod 30 and the number sleeve 60 in the distal direction against the bias of clutch spring 130 and in the opposite proximal direction under the bias of clutch spring 130. At least one longitudinal spline of the driver 40 engages a corresponding track of the lead screw 30.

A splined tooth interface with the housing 10 prevents rotation of the drive sleeve 40 during dose setting. This interface comprises a ring of radially extending outer teeth at the distal end of drive sleeve 40 and corresponding radially extending inner teeth of the housing component 10. When the button 70 is pressed, these drive sleeve 40 to housing 10 spline teeth are disengaged allowing the drive sleeve 40 to rotate relative to housing 10. A further splined tooth interface with the number sleeve 60 is not engaged during dialling, but engages when the button 70 is pressed, preventing relative rotation between the drive sleeve 40 and number sleeve 60 during dispense. In a preferred embodiment this interface comprises inwardly directed splines on a flange on the inner surface of the number sleeve 60 and a ring of radially extending outer splines of drive sleeve 40. These corresponding splines are located on the number sleeve 60 and the drive sleeve 40, respectively, such that axial movement of the drive sleeve 40 relative to the (axially fixed) number sleeve 60 engages or disengages the splines to rotationally couple or decouple the drive sleeve 40 and the number sleeve 60.

The driver 40 has a threaded section providing a helical track for the nut 50, i.e. a thread 41 having a minor diameter and a major diameter. In addition, a last dose abutment or stop is provided which may be the end of the thread track or preferably a rotational hard stop for interaction with a corresponding last dose stop of nut 50, thus limiting movement of the nut 50 on the driver thread.

A further interface of the drive sleeve 40 comprises a ring of ratchet clutch teeth 42 located at the proximal end face of drive sleeve 40 and a ring of corresponding ratchet teeth on the clutch plate 120. The teeth 42 define an outer diameter of the hollow body of the drive sleeve 40.

The last dose nut 50 is located between the number sleeve 60 and the drive sleeve 40. It is rotationally constrained to the number sleeve 60, via a splined interface. It moves along a helical path relative to the drive sleeve 40, via a threaded interface, when relative rotation occurs between the number sleeve 60 and drive sleeve 40 which is during dialling only. As an alternative, the nut 50 may be splined to the driver 40 and threaded to the number sleeve 60. A last dose stop is provided on nut 50 engaging a stop of drive sleeve 40 when a dose is set corresponding to the remaining dispensable amount of medicament in the cartridge 100.

Figure 3:
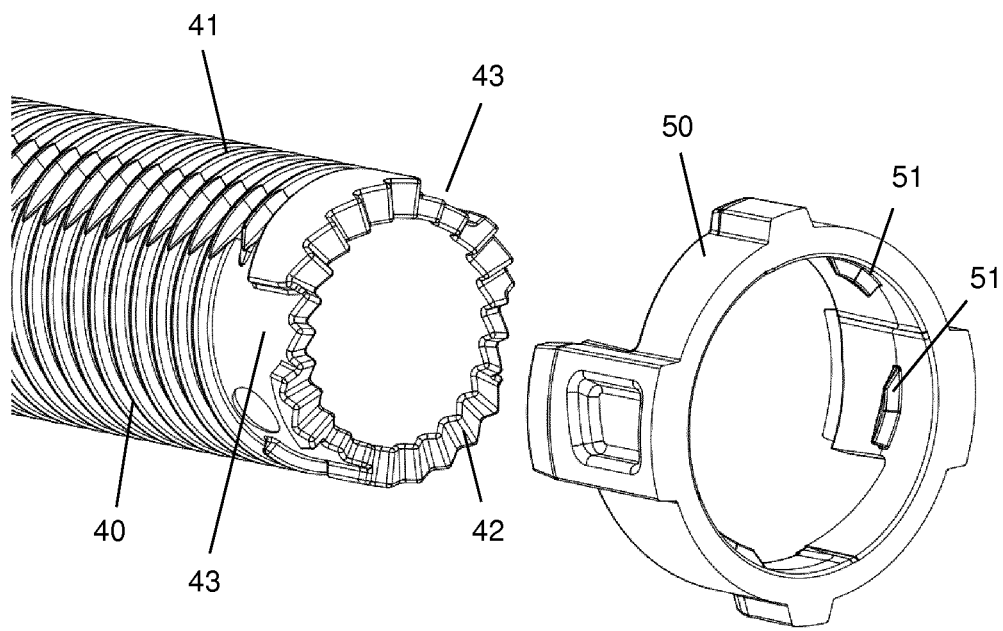
FIG. 3 shows the distal end of the drive sleeve of the device of FIG. 1 with the nut detached.

During assembly, the last dose nut 50 is inserted axially onto the driver 40. This is shown in FIG. 3. The last dose nut 50 has four small helical ribs or thread sections 51 on its internal diameter. The driver 40 clutch has four corresponding cut-outs 43 to allow these thread sections 51 to pass through. Providing the cavities or cut-outs 43 reduces the outer diameter of the body of the drive sleeve 40. In other words, the outer diameter of the drive sleeve 40 varies in regions with cavities 43 compared to regions without cavities. The depth of the cavities or cut-outs 43 is smaller than the major diameter of the thread 41 such that the thread sections 51 are allowed to pass over the (reduced) outer diameter of the body of the drive sleeve 40. In the embodiment shown in the Figures, the depth of the cavities or cut-outs 43 corresponds to the minor diameter of the thread 41.

Figure 4:
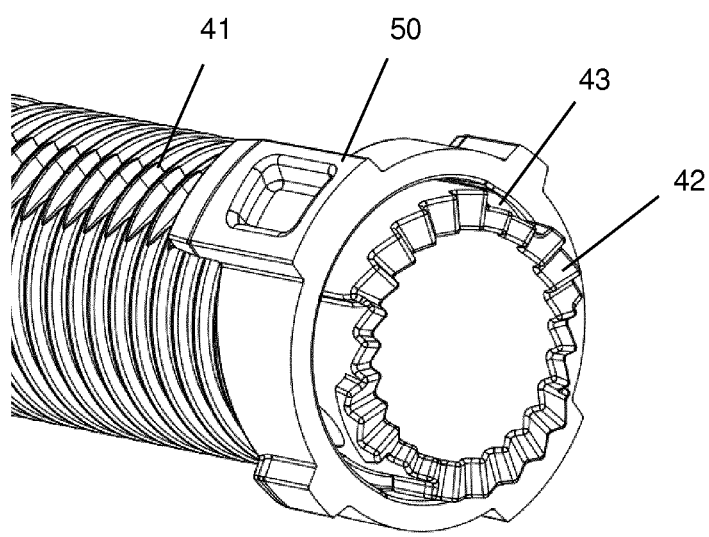
FIG. 4 shows the distal end of the drive sleeve of the device of FIG. 1 with the nut attached.

Once the mechanical sub-assembly is complete, a test dispense of e.g. three units is carried out. This causes the last dose nut 50 to rotate and engage the thread 41 on the driver 40 as shown in FIG. 4, removing the requirement for a separate rotational movement during assembly.

The use of small thread sections 51 on the last dose nut 50 minimises the size of the cut-outs 43 in the driver 40 clutch interface 42. These cut-outs 43 extend from the outer diameter of the clutch interface 42 which is the most effective region for transmitting torque. Therefore, by minimising the size of the cut-outs 43, the strength of the clutch interface 42 is maximised. Maximising the surface area of the clutch interface 42 also reduces the clutch surface wear rates.

The small thread sections 51 on the last dose nut 50 could be incorporated into any pen injector where their small size provided an advantage for another section of the mechanism. The method of using the test dispense to complete assembly of the last dose nut 50 could also be applied other pen injectors.

The dose indicator or number sleeve 60 is a tubular element. The number sleeve 60 is rotated during dose setting (via dose selector 80) and dose correction and during dose dispensing by torsion spring 90. The number sleeve 60 is axially constrained to the housing 10, e.g. by snap engagement of a bead on an inner housing surface with a groove on an outer number sleeve surface, while being free to rotate relative to the housing 10. The drive spring 90 is attached with one end to the number sleeve 60. Further, the number sleeve 60 is in threaded engagement with the gauge element 110 such that rotation of the number sleeve causes axial displacement of the gauge element 110. Together with gauge element 110 the number sleeve 60 defines a zero position ('at rest') and a maximum dose position. Thus, the number sleeve 60 may be seen as a dose setting member. The number sleeve 60 comprises a number sleeve lower 60*a* which is rigidly fixed to a number sleeve upper 60*b* during assembly, e.g. by snap engagement, to form the number sleeve 60.

Clutch features which have the form of a ring of splines are provided inwardly directed on number sleeve upper 60*b* for engagement with splines of the button 70 during dose setting and dose correction. A clicker arm is provided on the outer surface of number sleeve 60 which interacts with the drive sleeve 40 and the gauge member 110 for generating a feedback signal.

In addition, the number sleeve lower 60*a* is rotationally constrained to the nut 50 and to the clutch plate 120 via a splined interface comprising at least one longitudinal spline. Further, number sleeve lower 60*a* comprises an interface for attachment of the torsion spring 90.

The button 70 which forms the proximal end of the device is permanently splined to the dose selector 80. A central stem extends distally from the proximal actuation face of the button 70. The stem is provided with a flange carrying the splines for engagement with splines of the number sleeve upper 60*b*. Thus, it is also splined via splines to the number sleeve upper 60*b* when the button 70 is not pressed, but this spline interface is disconnected when the button 70 is pressed. The button 70 has a discontinuous annular skirt with splines. When the button 70 is pressed, splines on the button 70 engage with splines on the housing 10, preventing rotation of the button 70 (and hence the dose selector 80) during dispense. These splines disengage when the button 70 is released, allowing a dose to be dialled. Further, a ring of ratchet teeth is provided on the inner side of button flange for interaction with clutch plate 120.

The dose selector 80 is axially constrained to the housing 10. It is rotationally constrained, via the splined interface, to the button 70. This splined interface which includes grooves interacting with spline features formed by the annular skirt of button 70 remains engaged irrespective of the dose button 70 axial positions. The dose selector 80 or dose dial grip is a sleeve-like component with a serrated outer skirt.

The torsion spring 90 is attached at its distal end to the housing 10 and at the other end to the number sleeve 60. The torsion spring 90 is located inside the number sleeve 60 and surrounds a distal portion of the drive sleeve 40. The action of rotating the dose selector 80, to set a dose, rotates the number sleeve 60 relative to the housing 10, and charges the torsion spring 90 further.

The cartridge 100 is received in cartridge holder 20. The cartridge 100 may be a glass ampoule having a moveable rubber bung at its proximal end. The distal end of cartridge 100 is provided with a pierceable rubber seal which is held in place by a crimped annular metal band. In the embodiment depicted in the Figures, the cartridge 100 is a standard 1.5 ml cartridge. The device is designed to be disposable in that the cartridge 100 cannot be replaced by the user or health care professional. However, a reusable variant of the device could be provided by making the cartridge holder 20 removable and allowing back-winding of the lead screw 30 and the resetting of nut 50.

The gauge element 110 of FIGS. 1 and 2 is constrained to prevent rotation but allow translation relative to the housing 10 via a splined interface. The gauge element 110 has a helical feature on its inner surface which engages with the helical thread cut in the number sleeve 60 such that rotation of the number sleeve 60 causes axial translation of the gauge element 110. This helical feature on the gauge element 110 also creates stop abutments against the end of the helical cut in the number sleeve 60 to limit the minimum and maximum dose that can be set.

The gauge element 110 has a generally plate or band like component having a central aperture or window and two flanges extending on either side of the aperture. The flanges are preferably not transparent and thus shield or cover the number sleeve 60, whereas the aperture or window allows viewing a portion of the number sleeve lower 60*a*. Further, gauge element 110 has a cam and a recess interacting with the clicker arm of the number sleeve 60 at the end of dose dispensing.

The clutch plate 120 is a ring-like component. The clutch plate 120 is splined to the number sleeve 60 via splines. It is also coupled to the drive sleeve 40 via a ratchet interface. The ratchet provides a detented position between the number sleeve 60 and drive sleeve 40 corresponding to each dose unit, and engages different ramped tooth angles during clockwise and anti-clockwise relative rotation. A clicker arm is provided on the clutch plate 120 for interaction with ratchet features of the button 70.

The clutch spring 130 is a compression spring. The axial position of the drive sleeve 40, clutch plate 120 and button 70 is defined by the action of the clutch spring 130, which applies a force on the drive sleeve 40 in the proximal direction. This spring force is reacted via the drive sleeve 40, clutch plate 120, and button 70, and when 'at rest' it is further reacted through the dose selector 80 to the housing 10. The spring force ensures that the ratchet interface between drive sleeve 40 and clutch plate 120 is always engaged. In the 'at rest' position, it also ensures that the button splines are engaged with the number sleeve splines, and the drive sleeve teeth are engaged with teeth of the housing 10.

The bearing 140 is axially constrained to the piston rod 30 and acts on the bung within the liquid medicament cartridge. It is axially clipped to the lead screw 30, but free to rotate.

With the device in the 'at rest' condition as shown in FIG. 1, the number sleeve 60 is positioned against its zero dose abutment with the gauge element 110 and the button 70 is not depressed. Dose marking '0' on the number sleeve 60 is visible through the window of the housing 10 and gauge element 110, respectively.

The torsion spring 90, which has a number of pre-wound turns applied to it during assembly of the device, applies a torque to the number sleeve 60 and is prevented from rotating by the zero dose abutment.

The user selects a variable dose of liquid medicament by rotating the dose selector 80 clockwise, which generates an identical rotation in the number sleeve 60. Rotation of the number sleeve 60 causes charging of the torsion spring 90, increasing the energy stored within it. As the number sleeve 60 rotates, the gauge element 110 translates axially due to its threaded engagement thereby showing the value of the dialled dose. The gauge element 110 has flanges either side of the window area which cover the numbers printed on the number sleeve 60 adjacent to the dialled dose to ensure only the set dose number is made visible to the user.

A specific feature is the inclusion of a visual feedback feature in addition to the discrete dose number display typical on devices of this type. The distal end of the gauge element 110 creates a sliding scale through the window in the housing 10. As an alternative, the sliding scale could be formed using a separate component engaged with the number sleeve 60 on a different helical track.

As a dose is set by the user, the gauge element 110 translates axially, the distance moved proportional to the magnitude of the dose set. This feature gives clear feedback to the user regarding the approximate size of the dose set. The dispense speed of an auto-injector mechanism may be higher than for a manual injector device, so it may not be possible to read the numerical dose display during dispense. The gauge feature provides feedback to the user during dispense regarding dispense progress without the need to read the dose number itself. For example, the gauge display may be formed by an opaque element on the gauge element 110 revealing a contrasting coloured component underneath. Alternatively, the revealable element may be printed with coarse dose numbers or other indices to provide more precise resolution. In addition, the gauge display simulates a syringe action during dose set and dispense.

The drive sleeve 40 is prevented from rotating as the dose is set and the number sleeve 60 rotated, due to the engagement of its splined teeth with teeth of the housing 10. Relative rotation must therefore occur between the clutch plate 120 and drive sleeve 40 via the ratchet interface.

The user torque required to rotate the dose selector 80 is a sum of the torque required to wind up the torsion spring 90, and the torque required to overhaul the ratchet interface. The clutch spring 130 is designed to provide an axial force to the ratchet interface and to bias the clutch plate 120 onto the drive sleeve 40. This axial load acts to maintain the ratchet teeth engagement of the clutch plate 120 and drive sleeve 40. The torque required to overhaul the ratchet in the dose set direction is a function of the axial load applied by the clutch spring 130, the clockwise ramp angle of the ratchet teeth, the friction coefficient between the mating surfaces and the mean radius of the ratchet interface.

As the user rotates the dose selector 80 sufficiently to increment the mechanism by one increment, the number sleeve 60 rotates relative to the drive sleeve 40 by one ratchet tooth. At this point the ratchet teeth re-engage into the next detented position. An audible click is generated by the ratchet re-engagement, and tactile feedback is given by the change in torque input required.

Relative rotation of the number sleeve 60 and the drive sleeve 40 is allowed. This relative rotation also causes the last dose nut 50 to travel along its threaded path, towards its last dose abutment on the drive sleeve 40.

With no user torque applied to the dose selector 80, the number sleeve 60 is now prevented from rotating back under the torque applied by the torsion spring 90, solely by the ratchet interface between the clutch plate 120 and the drive sleeve 40. The torque necessary to overhaul the ratchet in the anti-clockwise direction is a function of the axial load applied by the clutch spring 130, the anti-clockwise ramp angle of the ratchet, the friction coefficient between the mating surfaces and the mean radius of the ratchet features. The torque necessary to overhaul the ratchet must be greater than the torque applied to the number sleeve 60 (and hence clutch plate 120) by the torsion spring 90. The ratchet ramp angle is therefore increased in the anti-clockwise direction to ensure this is the case whilst ensuring the dial-up torque is as low as possible.

The user may now choose to increase the selected dose by continuing to rotate the dose selector 80 in the clockwise direction. The process of overhauling the ratchet interface between the number sleeve 60 and drive sleeve 40 is repeated for each dose increment. Additional energy is stored within the torsion spring 90 for each dose increment and audible and tactile feedback is provided for each increment dialled by the re-engagement of the ratchet teeth. The torque required to rotate the dose selector 80 increases as the torque required to wind up the torsion spring 90 increases. The torque required to overhaul the ratchet in the anti-clockwise direction must therefore be greater than the torque applied to the number sleeve 60 by the torsion spring 90 when the maximum dose has been reached.

If the user continues to increase the selected dose until the maximum dose limit is reached, the number sleeve 60 engages with its maximum dose abutment on the maximum dose abutment of gauge element 110. This prevents further rotation of the number sleeve 60, clutch plate 120 and dose selector 80.

Depending on how many increments have already been delivered by the mechanism, during selection of a dose, the last dose nut 50 may contact its last dose abutment with stop face of the drive sleeve 40. The abutment prevents further relative rotation between the number sleeve 60 and the drive sleeve 40, and therefore limits the dose that can be selected. The position of the last dose nut 50 is determined by the total number of relative rotations between the number sleeve 60 and drive sleeve 40, which have occurred each time the user sets a dose.

With the mechanism in a state in which a dose has been selected, the user is able to deselect any number of increments from this dose. Deselecting a dose is achieved by the user rotating the dose selector 80 anti-clockwise. The torque applied to the dose selector 80 by the user is sufficient, when combined with the torque applied by the torsion spring 90, to overhaul the ratchet interface between the clutch plate 120 and drive sleeve 40 in the anti-clockwise direction. When the ratchet is overhauled, anti-clockwise rotation occurs in the number sleeve 60 (via the clutch plate 120), which returns the number sleeve 60 towards the zero dose position, and unwinds the torsion spring 90. The relative rotation between the number sleeve 60 and drive sleeve 40 causes the last dose nut 50 to return along its helical path, away from the last dose abutment.

With the mechanism in a state in which a dose has been selected, the user is able to activate the mechanism to commence delivery of a dose. Delivery of a dose is initiated by the user depressing the button 70 axially in the distal direction.

When the button 70 is depressed, splines between the button 70 and number sleeve 60 are disengaged, rotationally disconnecting the button 70 and dose selector 80 from the delivery mechanism, i.e. from number sleeve 60, gauge element 110 and torsion spring 90. Splines on the button 70 engage with splines on the housing 10, preventing rotation of the button 70 (and hence the dose selector 80) during dispense. As the button 70 is stationary during dispense, it can be used in the dispense clicker mechanism. A stop feature in the housing 10 limits axial travel of the button 70 and reacts any axial abuse loads applied by the user, reducing the risk of damaging internal components.

The clutch plate 120 and drive sleeve 40 travel axially with the button 70. This engages the splined tooth interface between the drive sleeve 40 and number sleeve 60, preventing relative rotation between the drive sleeve 40 and number sleeve 60 during dispense. The splined tooth interface between the drive sleeve 40 and the housing 10 disengages, so the drive sleeve 40 can now rotate and is driven by the torsion spring 90 via the number sleeve 60, and clutch plate 120.

Rotation of the drive sleeve 40 causes the piston rod 30 to rotate due to their splined engagement, and the piston rod 30 then advances due to its threaded engagement to the housing 10. The number sleeve 60 rotation also causes the gauge element 110 to traverse axially back to its zero position whereby the zero dose abutment stops the mechanism.

Tactile feedback during dose dispense is provided via the compliant cantilever clicker arm integrated into the clutch plate 120. This arm interfaces radially with ratchet features on the inner surface of the button 70, whereby the ratchet tooth spacing corresponds to the number sleeve 60 rotation required for a single increment dispense. During dispense, as the number sleeve 60 rotates and the button 70 is rotationally coupled to the housing 10, the ratchet features engage with the clicker arm to produce an audible click with each dose increment delivered.

Delivery of a dose continues via the mechanical interactions described above while the user continues to depress the button 70. If the user releases the button 70, the clutch spring 130 returns the drive sleeve 40 to its 'at rest' position (together with the clutch plate 120 and button 70), engaging the splines between the drive sleeve 40 and housing 10, preventing further rotation and stopping dose delivery.

During delivery of a dose, the drive sleeve 40 and number sleeve 60 rotate together, so that no relative motion in the last dose nut 50 occurs. The last dose nut 50 therefore travels axially relative to the drive sleeve 40 during dialling only.

Once the delivery of a dose is stopped, by the number sleeve 60 returning to the zero dose abutment, the user may release the button 70, which will re-engage the spline teeth between the drive sleeve 40 and housing 10. The mechanism is now returned to the 'at rest' condition.

At the end of dose dispensing, additional audible feedback is provided in the form of a 'click', distinct from the 'clicks' provided during dispense, to inform the user that the device has returned to its zero position via the interaction of the clicker arm on the number sleeve 60 with the ramp on the drive sleeve 40 and the cam and the recess on the gauge element 110. This embodiment allows feedback to only be created at the end of dose delivery and not created if the device is dialled back to, or away from, the zero position.

| Reference Numerals: | |
| --- | --- |
| 10 | housing (casing) |
| 20 | cartridge holder |
| 30 | piston rod (lead screw) |
| 40 | drive sleeve |
| 41 | thread |
| 42 | tooth |
| 43 | cut-out (cavity) |
| 50 | nut |
| 51 | thread section (helical rib) |
| 60 | dose setting element |
| 60a | number sleeve lower |
| 60b | number sleeve upper |
| 70 | button |
| 80 | dose selector |
| 90 | torsion spring |
| 100 | cartridge |
| 110 | gauge element |
| 120 | clutch plate |

| Reference Numerals: | |
| --- | --- |
| 130 | clutch spring |
| 140 | bearing |

The invention claimed is:

1. A drive sleeve with a hollow body having a clutch interface at a first end of the body and a thread extending on an outer surface of the body, wherein the clutch interface comprises a ring of crown teeth with a first outer diameter, the thread has a major diameter and a minor diameter, and the ring of crown teeth has at least two cavities extending on the outer surface of the body from the first end to the thread and defining a second outer diameter which is smaller than the major diameter of the thread, wherein the crown teeth are axially orientated and extend in a radial direction from an inner surface of the body to the outer surface of the body; and wherein each crown tooth has a first ramp angle orientated in a first rotational direction and a second, steeper ramp angle orientated in a second, opposite rotational direction.

2. The drive sleeve according to claim 1, wherein the second outer diameter defined by the cavities is equal to or smaller than the minor diameter of the thread.

3. The drive sleeve according to claim 1, wherein the cavities are slots extending in the axial direction of the body on the outer surface of the body.

4. The drive sleeve according to claim 1, comprising four non-equispaced cavities.

5. The drive sleeve according to claim 1, wherein at least one of the cavities ends in a start of the thread.

6. The drive sleeve according to claim 5, wherein the thread is a double-start thread with one of the cavities ending in each start of the thread.

7. The drive sleeve according to claim 1, further comprising at least one rotational hard stop located at an end of the thread which is opposite to the ring of crown teeth.

8. The drive sleeve according to claim 1, wherein the hollow body comprises at least one further clutch interface with axially orientated splines located on an inner surface or the outer surface of the body.

9. A drug delivery device for selecting and dispensing a number of user variable doses of a medicament, the drug delivery device comprising:

a drive sleeve with a hollow body, the drive sleeve comprising a clutch interface at a first end of the body and a thread extending on an outer surface of the body, wherein the clutch interface comprises a ring of crown teeth with a first outer diameter, the thread has a major diameter and a minor diameter, and the ring of crown teeth has at least two cavities extending on the outer surface of the body from the first end to the thread and defining a second outer diameter which is smaller than the major diameter of the thread, wherein the crown teeth are axially orientated and extend in a radial direction from an inner surface of the body to the outer surface of the body, and wherein each crown tooth has a first ramp angle orientated in a first rotational direction and a second, steeper ramp angle orientated in a second, opposite rotational direction, a housing, a dose setting member located within the housing, a piston rod engaging the drive sleeve, a clutch having a further ring of crown teeth for rotationally coupling and de-coupling the drive sleeve and the dose setting member, and a nut having at least one helical inner rib for engaging the thread of the drive sleeve, wherein the width of the helical inner rib is equal to or smaller than the width of one of the cavities.

10. The drug delivery device according to claim 9, further comprising a cartridge containing a medicament.

11. A method for assembling a drug delivery device for selecting and dispensing a number of user variable doses of medicament, the method comprising:

providing components of the drug delivery device, the components comprising a drive sleeve with a hollow body having a clutch interface at a first end of the body and a thread extending on an outer surface of the body, wherein the clutch interface comprises a ring of crown teeth with a first outer diameter, the thread has a major diameter and a minor diameter, and the ring of crown teeth has at least two cavities extending on the outer surface of the body from the first end to the thread and defining a second outer diameter which is smaller than the major diameter of the thread, wherein the crown teeth are axially orientated and extend in a radial direction from an inner surface of the body to the outer surface of the body, and wherein each crown tooth has a first ramp angle orientated in a first rotational direction and a second, steeper ramp angle orientated in a second, opposite rotational direction, a housing, a dose setting member configured to be located within the housing, a piston rod configured to engage the drive sleeve, a clutch having a further ring of crown teeth for rotationally coupling and de-coupling the drive sleeve and the dose setting member, and a nut having at least one helical inner rib for engaging the thread of the drive sleeve, wherein the width of the helical inner rib is equal to or smaller than the width of one of the cavities, inserting the nut onto the drive sleeve in an axial movement, whereby the at least one helical inner rib of the nut engages a cavity of the at least two cavities of the drive sleeve, and performing a relative rotational movement between the drive sleeve and the nut, until the at least one helical inner rib engages the thread of the drive sleeve.

12. The method according to claim 11, comprising performing a test dispense after assembling the piston rod, the drive sleeve, the nut, the dose setting member and the clutch into the housing, wherein the relative rotational movement between the drive sleeve and the nut is performed during the test dispense.

13. The method according to claim 11, further comprising engaging the nut with the dose setting member such that the nut is axially displaceable and rotationally constrained to the dose setting member.

\* \* \* \* \*